(12) United States Patent
Maschke

(10) Patent No.: US 6,772,001 B2
(45) Date of Patent: Aug. 3, 2004

(54) MEDICAL EXAMINATION AND/OR TREATMENT SYSTEM

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 10/346,612

(22) Filed: Jan. 17, 2003

(65) Prior Publication Data
US 2003/0144590 A1 Jul. 31, 2003

(30) Foreign Application Priority Data
Jan. 29, 2002 (DE) .......................................... 102 03 372

(51) Int. Cl.[7] ................................................. A61B 5/05
(52) U.S. Cl. ........................ 600/423; 600/434; 600/467
(58) Field of Search .............................. 600/422–425, 600/434, 435, 462, 466, 463, 467; 604/528

(56) References Cited

U.S. PATENT DOCUMENTS

| | | | | |
|---|---|---|---|---|
| 4,134,405 A | * | 1/1979 | Smit | 606/108 |
| 5,243,988 A | * | 9/1993 | Sieben et al. | 600/463 |
| 5,269,759 A | * | 12/1993 | Hernandez et al. | 604/96.01 |
| 5,334,207 A | * | 8/1994 | Gay, Jr. | 606/7 |
| 5,353,795 A | * | 10/1994 | Souza et al. | 600/423 |
| 5,431,640 A | * | 7/1995 | Gabriel | 604/270 |
| 5,509,044 A | * | 4/1996 | Horbaschek | 378/97 |
| 5,542,938 A | * | 8/1996 | Avellanet et al. | 604/528 |
| 5,630,427 A | * | 5/1997 | Hastings | 604/524 |
| 5,706,827 A | * | 1/1998 | Ehr et al. | 600/585 |
| 5,813,996 A | * | 9/1998 | St. Germain et al. | 600/585 |
| 6,126,647 A | * | 10/2000 | Posey et al. | 604/270 |
| 6,280,385 B1 | * | 8/2001 | Melzer et al. | 600/423 |
| 6,298,261 B1 | | 10/2001 | Rex | |
| 6,321,109 B2 | * | 11/2001 | Ben-Haim et al. | 600/424 |
| 6,385,472 B1 | * | 5/2002 | Hall et al. | 600/374 |
| 6,408,202 B1 | * | 6/2002 | Lima et al. | 600/423 |
| 6,505,062 B1 | * | 1/2003 | Ritter et al. | 600/407 |
| 6,507,751 B2 | * | 1/2003 | Blume et al. | 600/424 |
| 6,524,303 B1 | * | 2/2003 | Garibaldi | 604/525 |
| 6,690,963 B2 | * | 2/2004 | Ben-Haim et al. | 600/424 |
| 6,704,594 B1 | * | 3/2004 | Blank et al. | 600/423 |
| 2003/0135111 A1 | * | 7/2003 | Meaney et al. | 600/422 |

FOREIGN PATENT DOCUMENTS

DE  OS 40 37 586  5/1992

* cited by examiner

Primary Examiner—Mary Beth Jones
Assistant Examiner—Ruby Jain
(74) Attorney, Agent, or Firm—Schiff Hardin LLP

(57) ABSTRACT

A medical examination and/or treatment system has an X-ray image exposure system with a radiation source, a radiation receiver as well as a control and processing device that controls them, a catheter system with a catheter with at least one element in the catheter tip that generates a magnetic field and a device for generating an external magnetic field for guiding the movement of the catheter introduced into a patient by interaction with the magnetic field generated by the element at the catheter tip, as well as an ultrasound image exposure system having a device integrated in the catheter tip for generating and for receiving ultrasound and having a control and processing device that controls this device.

13 Claims, 2 Drawing Sheets

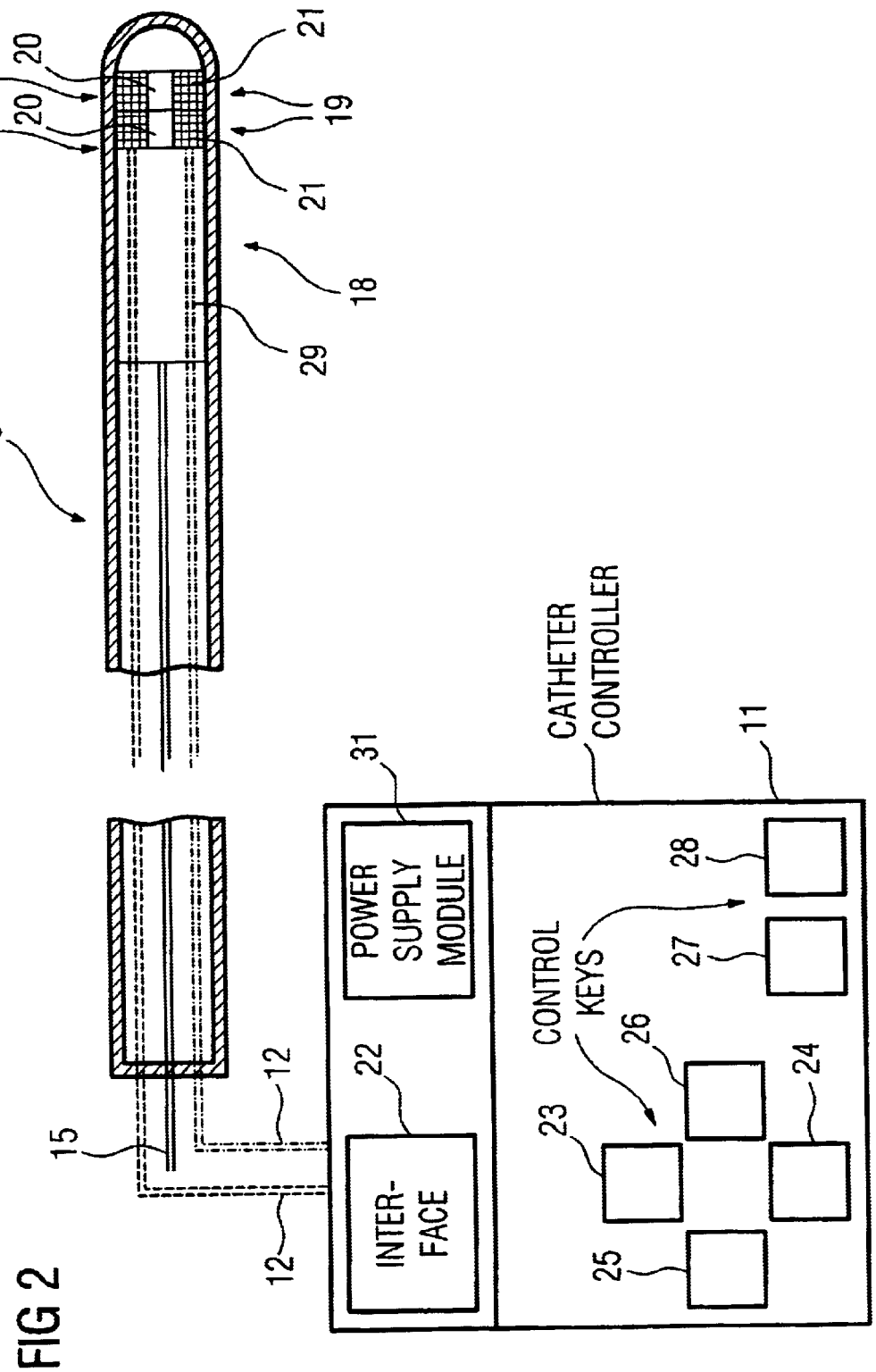

MEDICAL EXAMINATION AND/OR TREATMENT SYSTEM

BACKGROUND OF THE INVENTION

1. Field of the Invention

The present invention is directed to a medical examination and/or treatment system of the type employing a catheter that is guided in the body of an examination or treatment subject.

2. Description of the Prior Art

Cardiac infarction is caused by diseases of the arterial coronary vessels (arterial sclerosis). Deposits (arterial sclerotic plaque) at the vessel wall lead to a reduction in the vessel diameter and ultimately can produce blockage of individual or a number of coronary vessels. It has been recognized that the risk of suffering a cardiac infarction is not primarily dependent on the reduction of the vessel diameter. On the contrary, it is also important whether the thin protective layer that covers the arterial sclerotic deposit is intact. When this breaks apart, then thrombocytes collect at the point of rupture, which completely close the vessel within a short time and thus causing the cardiac infarction.

A catheter has been conventional employed for examination or treatment of this condition, the catheter being advanced into the region of the endangered coronary vessel with simultaneous X-ray monitoring for identifying the position of the catheter and for monitoring the examination/treatment. The physician manually introduces such a catheter into the vessel system and displaces it therein. Even though the catheter is flexible, problems arise due to this manual guidance, particularly in the region of vessel bends and the like. The movement and positioning of the catheter, consequently, is problematical. A perforation of the vessel wall can occur if the tip of the catheter is too forcefully pressed thereagainst, as can easily occur due to the tight tolerances in the directional movement.

Another problem associated with procedures of this type is that the simultaneous X-ray monitoring supplies only information about the free volume, i.e. the unfilled volume, of the vessel but does not supply any information about the vessel wall and thus the problematical plaque deposits themselves. Although known examination and/or treatment systems supply important information for the physician, they do not supply all information required in the optimum case for an exact diagnosis.

German OS 40 37 586 discloses a medical probe for examining a body that emits electromagnetic waves that are acquired by a receiver arranged outside the body, from which the probe can be localized. An image of the probe can be displayed in an X-ray image, for example.

U.S. Pat. No. 6,298,261 discloses a catheter tracking system. A number of transducers are employed as locating aid, one of these being arranged on the head of the catheter.

These systems only serve for locating a catheter. The aforementioned problems in the manual movement of the catheter by a physician continue to exist. Moreover, the physician is not provided with any further information by these locating systems.

SUMMARY OF THE INVENTION

An object of the present invention is to provide an examination and/or treatment system that is improved compared to the above-discussed systems.

This object is achieved in accordance with the invention in an examination and/or treatment system having an X-ray image exposure system with a radiation source, a radiation receiver as well as a control and processing device that controls them. a catheter system having a catheter with at least one element that is provided in the catheter tip that generates a magnetic field and a device for generating an external magnetic field for guiding movement of the catheter within a patient, as well as an ultrasound image exposure system having a device integrated in the catheter tip for generating and for receiving ultrasound and having a control and processing device that controls this device.

The inventive system makes use of the known technique of monitoring the catheter movement as well as the vessel volume using an X-ray image exposure system. A simple or a bi-planar C-arm device, for example, can be utilized. The inventive system, further, employs a catheter system with a catheter that is not guided manually but is guided by means of a magnetic field generated externally of the patient. To this end, an element that generates a magnetic field at the catheter side is provided in the catheter tip. This magnetic field generated in the patient interacts with the external navigation or guidance magnetic field, which is modified for moving the catheter in terms of its position relative to the patient. In this way, directional control can be implemented quasi actively in the region of the catheter tip, which must necessarily be guided first around any vessel bends or the like, so that the catheter movement is significantly simpler and significantly more precise with respect to the positioning.

An ultrasound image exposure system also is utilized, the sound generation and reception device thereof being integrated in the catheter tip. Ultrasound images are directly registered from the inside of the vessel, showing the vessel wall in detail, so that the attending physician is provided with information about the appearance of the vessel wall.

Overall, the inventive system offers a number of advantages, namely a simple and extremely precise mobility and positionability of the catheter, as well as the availability of different images, namely the X-ray images showing the free vessel volume and the ultrasound images showing the detailed inside vessel wall and vessel structure. The physician thus is provided with image information that is important and should be combined for the diagnosis and that is essential for the correct treatment.

In an embodiment of the invention the X-ray images and the ultrasound images can be displayed at a common monitor, preferably simultaneously, so the physician can immediately combine the two images showing the same examination region with one another or compare them and process them in terms of image processing insofar as this is necessary.

For a simple operation of the treatment system with its various components, it is expedient to integrate the controller of the X-ray system and the controller of the ultrasound system and the controller of the device that generates the external magnetic field in a common control device, so that the operation of these sub-systems can ensue proceeding from a single control console.

It is especially expedient for the magnetic field of the catheter that is generated via the magnetic field-generating elements in the catheter tip to be variable given a catheter introduced into a patient, i.e. variable in field strength and/or field direction. In this way, the interaction of the magnetic field of the catheter side generated therewith with the external magnetic field can be varied. An electromagnet with a core and a coil is expediently employed as the element that generates the magnetic field, with the leads of the coil being guided in the catheter sheath so the coil can be energized in controlled fashion from outside the patient via a catheter control device. A field variation is possible in a simple way by a suitable control of the coil current. The field strength can be increased by increasing the current; the field direction changes due to a reversal of the direction of the current, etc. This control can ensue in a simple way if the catheter control device is fashioned as a separate, for example portable, device, so that it can be positioned close to the patient and long leads—at least to the coils—can be foregone. Of course, it is also conceivable to likewise integrate the catheter controller in the aforementioned common control device.

It is expedient to employ two or more electromagnets in order to obtain an additional degree of freedom of the field variation by superimposing the individual fields, given individually controllable electromagnets. It is also possible to drive at least some of the multiple electromagnets in common.

In a further embodiment of the invention the (at least one) electromagnet is arranged such that the magnetic field that can it generates resides essentially parallel to the longitudinal axis of the catheter. Alternatively, the (at least one) electromagnet can be arranged such that the magnetic field it generates resides essentially perpendicular to the longitudinal axis of the catheter. A different interaction with the external field (given an assumed, same field direction of the external field) derives dependent on what the field direction is, i.e. the force that is generated therewith and acts on the catheter tip is directed differently.

In a further embodiment at least two electromagnets arranged in this way are provided, with the magnetic field generated by one electromagnet residing essentially parallel and the magnetic field generated by the other electromagnet residing essentially perpendicular to the longitudinal axis of the catheter, so that both of the aforementioned guidance possibilities can be utilized. Additionally, at least one permanent magnet element can be provided in the region of the catheter tip, so that the operation of the electromagnet or electromagnets can be foregone, at least temporarily, if the magnetic field of this at least one permanent magnet element suffices for the movement.

In another embodiment of the invention the catheter controller communicates with the controller for generating the external magnetic field, and the control of the electromagnet or electromagnets ensues dependent on the control information of the magnetic field generating device. The catheter controller thus can react to changes in the momentary setting parameters of the magnetic field generating device or take these into consideration in the context of the control of the coil current, so that the supply of the coils with current always ensues according to the desired interaction.

DESCRIPTION OF THE DRAWINGS

FIG. 2 is a schematic illustration of a catheter with allocated catheter controller for use in the inventive system.

DESCRIPTION OF THE PREFERRED EMBODIMENTS

Figure 1:
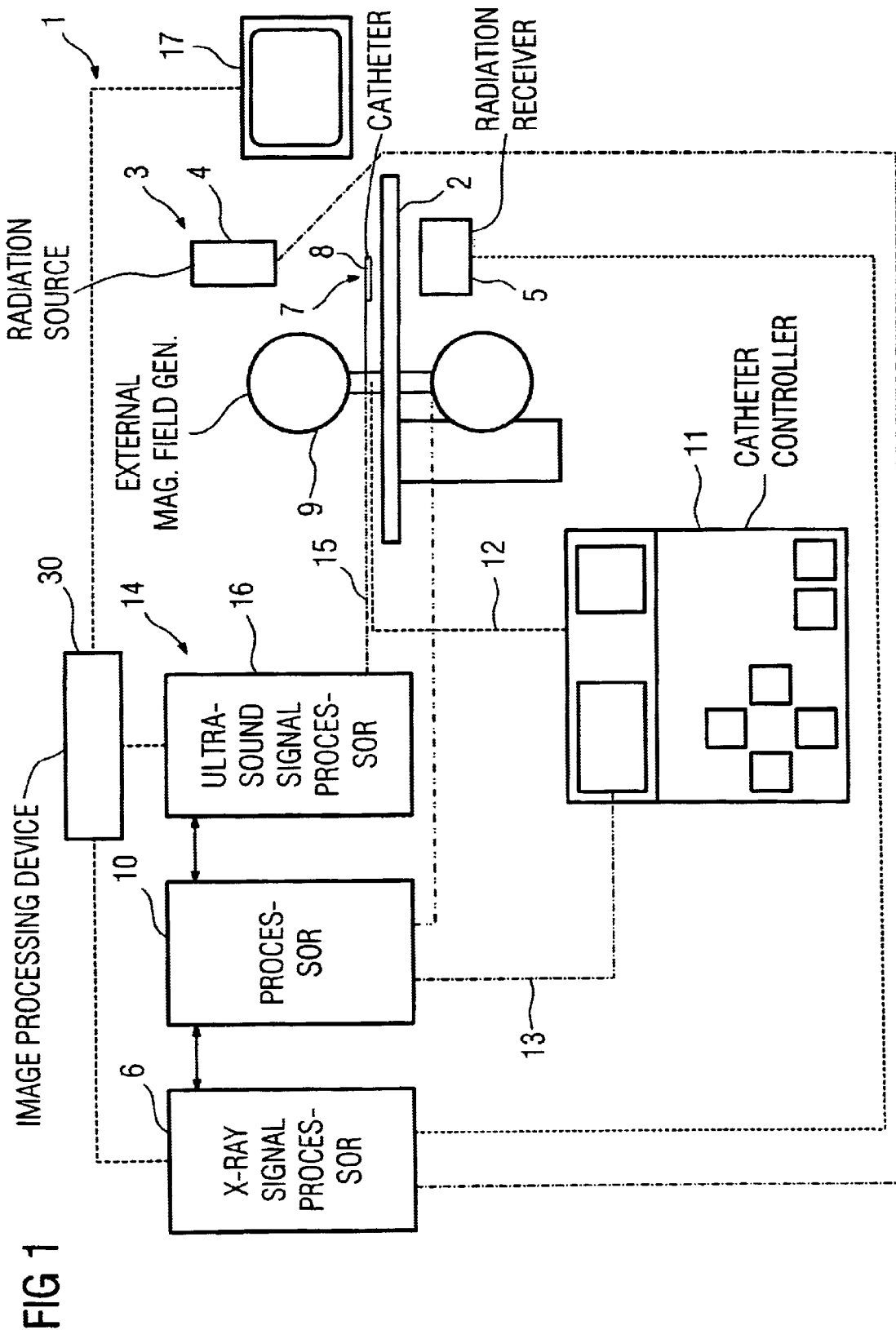
FIG. 1 is a schematic illustration of the inventive examination and/or treatment system.

FIG. 1 shows a schematic illustration of an inventive examination and/or treatment system 1 with which a patient (not shown in detail) located on a patient support table 2 can be examined/treated. The system has an X-ray imaging system 3 with a radiation source 4 for generating X-rays, a radiation receiver, for example a flat image detector 5, for registering radiation images, as well as a control and processing device 6 that controls the operation of the radiation source 4, the radiation receiver 5 as well as the spatial motion and positioning thereof Further, a catheter system 7 is provided having a catheter 8 that is to be introduced into a patient, which has a magnetic field-generating element (discussed in greater detail with reference to FIG. 2) arranged in its tip, and further having a device 9 for generating a patient-external magnetic field that interacts with the magnetic field generated in the catheter tip in order to thus move the catheter 8 through the vessel of the patient. The catheter system also has a control and processing device 10 via which the operation of the device 9 generating the external magnetic field is controlled.

The catheter system also has a catheter controller 11 that is connected via at least one line connection 12 to at least one coil of an electromagnet arranged in the catheter tip via which the magnetic field at the catheter is generated, by means of which the coil can be provided with current. The catheter controller 11 is also in communication with the control and processing device 10 via a communication line 13 or wireless communication can be used ensue.

An ultrasound imaging system 14 also is provided, having an ultrasound generating and reception device that is likewise integrated in the catheter tip, discussed below. This device is connected via a line connection 15 to a control and processing device 16 wherein the ultrasound image data are processed.

The image signals picked up by the radiation receiver 5 and forwarded to the control and processing device 6 as well as the image signals registered by the ultrasound generating and reception device 29 and forwarded to the control and processing device 16 are processed in common in a digital image processing device 30. A monitor 17 is also provided, the X-ray images and ultrasound images generated by the image processing device 30 being output thereat, preferably in common.

FIG. 2 shows the catheter 8 in detail. In the illustrated example, two electromagnets 19 each composed of a core 20 and of a coil 21 are arranged in the catheter tip. The coils can be separately provided with power via the two leads 12 so the electromagnets 19 can be separately operated.

For the purpose of providing power, the catheter controller 11 has a power supply module 31 available to it. An interface 22 is also provided via which the communication with the control and processing device 10 for the magnetic field-generating device 9 ensues. Thus the catheter controller 11 always has the momentary (current) control information available to it, the external magnetic field being generated dependent thereon and on the basis whereof the intensity and direction thereof and other relevant information that can be acquired. The power delivery to the coils 20 can then be controlled dependent on this information.

Due to the arrangement of the two electromagnets 19, a magnetic field generated thereby is always directed in the direction of the longitudinal axis. The direction of the magnetic field can be reversed dependent on the direction of the coil current, i.e. the polarity can be swtiched. Different interactions are possible dependent on how the external magnetic field is directed relative to the internal magnetic field. When the external magnetic field lies parallel to the internal magnetic field, then—dependent on the field alignment—a forward displacement or a reverse displacement can ensue by moving the external magnetic field. The catheter follows the movement of the external magnetic field as a result of the magnetic interaction. A quasi longitudinal sliding motion ensues when the two fields are identically directed.

When the external field resides perpendicular to the internal field, then the internal field attempts to turn in the direction of the external field. Thus it is possible to initiate a swiveling or bending motion with a bending toward the right or left or upward or downward being dependent on how the respective directions of the external and internal magnetic fields reside relative to one another. The internal magnetic field always attempts to turn into the same direction as the external magnetic field.

As an alternative to the arrangement of the electromagnets shown in FIG. 2, it is also possible to orient them at an angle of 90° compared to the orientation shown in FIG. 2, so the internal magnetic field resides essentially perpendicular to the longitudinal axis of the catheter. When the external magnetic field likewise resides perpendicular to the longitudinal axis of the catheter but, for example, offset by 90° relative to the internal magnetic field, then a rotational motion around the longitudinal axis of the catheter can be initiated, since the internal magnetic field also strives to follow the external magnetic field and become aligned with it. This rotational motion ensues until the internal field lies in the same direction as the external. Use is made of the principle known from an electric motor in order to turn the catheter a short distance in a stationary external field. Here as well, a rotation toward the left or right is possible dependent on how the external field resides relative to the internal field.

In order to setting the internal field to implement the motion of the catheter that the physician wants, various operating elements, for example control keys, 23 through 28 are provided at the catheter controller. The key 23 stands for "forward", the key 24 for, for example, "reverse". When, for example, the key 23 is pressed, then a coil current is selected in terms of its direction so that an internal magnetic field is generated that is directed the same as the external magnetic field, so that the catheter is likewise shifted toward the right given, for example, a movement of the external magnetic field toward the right. When the catheter is to be pulled back, then, first, the external magnetic field is correspondingly repolarized. The same is true of the infernal magnetic field, which is automatically initiated be pressing the control element 24. The catheter controller 11 receives the information about how the coil current is to be selected via the interface 22 on the basis of the control information of the control and processing device 10.

Bending motion toward the left or right ensues in a corresponding way. This is initiated when the control elements 25 or 26 are pressed. Based on the knowledge about that direction perpendicular to the longitudinal axis of the catheter wherein the external field resides, the internal field is correspondingly generated by selecting the direction of the current, so that the corresponding bending toward the right or left occurs due to the interaction of the internal field relative to the external field.

When a rotation toward the left or right around the longitudinal axis of the catheter is to be initiated, then the control elements 27, 28 are actuated. These drive a further electromagnet (not shown) that in the illustrated example is arranged perpendicular to the electromagnet 19 and that generates a magnetic field perpendicular to the longitudinal catheter axis is driven. Here as well, the selection of the direction of the coil current ensues dependent on the information about the external magnetic field or its direction.

A device 29 for generating and for receiving ultrasound waves is also provided at the catheter. This device 29 is likewise integrated in the catheter tip. Via a connecting line 15, the device 29 communicates with the control and processing device 16, where the ultrasound reception signals, i.e. ultimately the ultrasound image data, are registered.

For examining or treating a patient, the catheter is first introduced into the patient at a suitable introduction point; subsequently, it is guided via the external magnetic field in interaction with the internal magnetic field and can thus be guided exactly into the examination region. This ensues under continuous X-ray monitoring with the X-ray imaging system 3, with the X-ray images being displayed at the monitor 17. The ultrasound image pick-up via the ultrasound exposure system 14 can ensue simultaneously during the entire motion path of the catheter, whether during insertion or upon withdrawal, so information about the specific appearance of the inside vessel wall is also continuously received. These ultrasound images likewise are displayed at the common monitor 17.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical system for examination or treatment of a patient, comprising:

an x-ray imaging system comprising a radiation source, a radiation receiver, and an x-ray control and processing device for controlling said radiation source and said radiation receiver and for generating signals representing an x-ray image of a patient;

a catheter system comprising a catheter adapted for insertion in said patient, said catheter having a catheter tip at which an element is disposed which generates a magnetic field, and a magnetic field generating device for generating a magnetic field externally of said patient for interacting with said magnetic field generated by said element at said catheter tip for moving said catheter within said patient; and an ultrasound imaging system including an ultrasound element integrated at said catheter tip for generating and receiving ultrasound, and an ultrasound control and processing device connected to said ultrasound element for generating signals representing an ultrasound image.

2. A medical system as claimed in claim 1 further comprising a monitor supplied with said signals representing said x-ray image and said signals representing said ultrasound image for displaying said x-ray image and said ultrasound image.

3. A medical system as claimed in claim 2 wherein said monitor displays said x-ray image and said ultrasound image in common.

4. A medical system as claimed in claim 1 further comprising a magnetic field generator control device for controlling generation of said external magnetic field by said magnetic field generator, and wherein said x-ray control device, said ultrasound control device and said magnetic field generator control device are integrated in a common control device.

5. A medical system as claimed in claim 1 further comprising a catheter control device for controlling said magnetic field generated by said element at said catheter tip while said catheter is disposed in said patient.

6. A medical system as claimed in claim 5 wherein said element comprises an electromagnet having a core and a coil said coil having leads conducted to said control device externally of said patient.

7. A medical system as claimed in claim 6 comprising at least one further electromagnet for generating said magnetic field at said catheter tip.

8. A medical system as claimed in claim 7 wherein said further electromagnet is connected to said catheter control device and wherein said electromagnet and said further electromagnet are selectively driveable individually or in common.

9. A medical system as claimed in claim 7 wherein said catheter has a longitudinal axis, and wherein at least one of said electromagnet and said further electromagnet is oriented for generating said magnetic field at said catheter tip substantially parallel to said longitudinal axis.

10. A medical system as claimed in claim 7 wherein said catheter has a longitudinal axis, and wherein at least one of said electromagnet and said further electromagnet is oriented for generating said magnetic field at said catheter tip substantially perpendicular to said longitudinal axis.

11. A medical system as claimed in claim 7 wherein said catheter has a longitudinal axis and wherein said electromagnet is oriented for generating a magnetic field substantially parallel to said longitudinal axis and wherein said further electromagnet is oriented for generating a magnetic field substantially perpendicular to said longitudinal axis.

12. A medical system as claimed in claim 1 wherein said element comprises at least one permanent magnet.

13. A medical system as claimed in claim 1 further comprising a catheter control unit connected to said electromagnet and a magnetic field generator control unit connected to said magnetic field generator, said magnetic field generator control unit being supplied with control information and said catheter control unit being connected to said magnetic field generator control unit for controlling generation of said magnetic field at said catheter tip dependent on said control information as well.

* * * * *